United States Patent [19]
Carlson et al.

[11] Patent Number: 4,713,618
[45] Date of Patent: Dec. 15, 1987

[54] ON-LINE CALIBRATION SYSTEM FOR CHEMICAL MONITORS

[75] Inventors: Gerald L. Carlson, Mt. Lebanon Township, Allegheny County; David F. Pensenstadler, N. Huntingdon; Warren E. Snider, Elizabeth Township, Allegheny County; William A. Byers, Pittsburgh, all of Pa.

[73] Assignee: Westinghouse Electric Corp., Pittsburgh, Pa.

[21] Appl. No.: 782,858

[22] Filed: Oct. 2, 1985

[51] Int. Cl.⁴ .......................................... G01N 27/56
[52] U.S. Cl. ................................. 324/438; 73/1 R; 204/400; 324/450
[58] Field of Search ................... 324/438, 439, 450; 204/400, 433; 73/1 R

[56] References Cited

U.S. PATENT DOCUMENTS

| | | | |
|---|---|---|---|
| 3,839,162 | 10/1974 | Ammer | 204/1 T |
| 3,884,640 | 5/1975 | Lock et al. | 324/438 X |
| 3,941,665 | 3/1976 | Eckfeldt et al. | 324/438 |
| 4,151,255 | 4/1979 | Capuano et al. | 324/438 |
| 4,329,649 | 5/1982 | Scoates | 324/438 |
| 4,384,925 | 5/1983 | Stetter et al. | 204/1 T |
| 4,414,858 | 11/1983 | Peterson et al. | 73/863.33 |
| 4,473,458 | 9/1984 | Schwartz et al. | 73/1 R |
| 4,476,712 | 10/1984 | Carlson et al. | 73/61.1 C |
| 4,490,236 | 12/1984 | Petty | 73/1 R |

*Primary Examiner*—Reinhard J. Eisenzopf
*Assistant Examiner*—Robert W. Mueller

[57] ABSTRACT

An on-line calibration system for calibrating chemical monitors which monitor a selected chemical characteristics of a fluid sample stream, including a conditioning system for conditioning an influent fluid sample stream to produce a conditioned fluid sample stream having a predetermined level of the selected chemical characteristic. By exposing a sensor of the monitor to the conditioned fluid sample stream and calibrating the response of the sensor with respect to the predetermined level of the selected chemical characteristic in the conditioned fluid sample stream, this calibration system eliminates the effects on the response of the sensor of any ionic species in the fluid sample stream which do not affect the chemical characteristic being monitored. The on-line calibration system also includes a system which is selectively operable to establish first and second fluid sample stream flow paths, the first flow path providing the influent fluid sample stream to the detector for monitoring of the selected chemical characteristic, and the second flow path providing the influent fluid sample stream to the conditioning system and the conditioned fluid sample stream to the detector for calibrating the monitor.

15 Claims, 9 Drawing Figures

ON-LINE CALIBRATION SYSTEM FOR CHEMICAL MONITORS

BACKGROUND OF THE INVENTION

1. Field of the Invention

The present invention relates to an on-line calibration system for calibrating chemical monitors which analyze a fluid sample, and more particularly, to a calibration system which conditions a portion of the fluid sample to be analyzed by the chemical monitor to a predetermined chemical characteristic so that the chemical monitor is calibrated with respect to the predetermined chemical characteristic of the conditioned portion of the fluid sample.

2. Description of the Related Art

The control of impurities in and the chemical characteristics of power plant steam cycle water is recognized as an important and necessary measure in protecting a power plant against corrosion related failures and insuring plant reliability. Various on-line monitors are available for detecting chemicals and chemical characteristics, including dissolved oxygen, pH, sodium, hydrazine, ammonia, specific conductivity, and cation conductivity, in a flowing fluid sample, e.g., a stream of steam cycle water. For accurate control of the chemical characteristics of steam cycle water, on-line monitors must be calibrated on a regular basis.

In order to accurately calibrate a chemical monitor, it is necessary to eliminate or compensate for the effects of any ionic, or chemical, species in the fluid sample, other than the chemical characteristic being monitored, which vary the response of the monitor but which do not alter the particular chemical characteristic being monitored. Further, the sensors and electrodes used in conjunction with many monitors respond differently in a stagnant solution than in a flowing stream. Thus, accurate calibration requires that the sensor be placed in a flowing stream during calibration. In addition, it is desirable to have an in situ calibration procedure which can be automated since monitors are located in a variety of different locations in a power plant and since it is mandatory to confirm that the information generated by on-line monitors is accurate and reliable whenever a steam process disturbance is detected.

Calibration of chemical monitors, for example, pH monitors, historically has been accomplished with an off-line procedure using concentrated buffer solutions. In calibrating a pH monitor, a pH electrode is placed in the buffer solution and a pH meter is set to the known pH of the buffer solution. Then, the electrode is returned to a flow cell to detect the pH of a flowing sample. Re-calibration requires the manual removal of the electrode from the flow cell to place the pH electrode in the buffer solution. However, such an off-line calibration procedure is difficult to automate and fails to eliminate the effects of ionic species in the fluid sample which do not affect chemical characteristics being monitored, but which do have an effect on the response of the sensor or electrode used to perform the monitoring, thereby creating an erroneous pH measurement when the pH electrode is used to analyze the fluid sample. Off-line calibration using a buffer solution is often inaccurate for three further reasons: first, flowing fluid samples influence the response of a sensor or electrode differently than stagnant solutions; second, many sensors and electrodes tend to respond differently in buffer solutions than they do in high-purity fluid samples having minimal buffering capacity; and third, temperature differences between the buffer solution and the fluid sample are not accounted for in the calibration procedure.

Various systems have been proposed to calibrate chemical monitors. For example, a pH monitor having an automatic buffer standardization system for automatically, periodically standardizing the monitor against a buffer solution of a known pH is disclosed in U.S. Pat. No. 4,151,255-Capuano et al. In this system, the pH measuring means has pH electrodes which are located in a test chamber. During a pH measurement, sample fluid is fed to the test chamber. To calibrate the pH measuring means, the sample fluid is drained from the test chamber, the test chamber is rinsed with a rinse fluid, and then a buffer solution is introduced into the test chamber. Thus, the pH measuring means can be adjusted with respect to the known pH of the buffer solution. This system, however, does not eliminate or compensate for ionic species in the sample fluid which have an effect on the response of the pH electrode, nor does it address the problem of variations in the response of a pH electrode to a concentrated buffer solution versus a high purity fluid sample having minimal buffering capacity. Further, during a measurement, the sample fluid fed to the test chamber accumulates therein and exits only through an overflow opening. Thus, the pH electrode responds to the pH of the entire volume of sample fluid collected in the test chamber over a period of time, rather than the pH of the sample fluid provided to the test chamber at any one point in time. Accordingly, the pH measurement provided by this system is a profile of the pH of the fluid sample provided to the test chamber over a period of time and instantaneous or continuous on-line measurements of the pH of a particular portion of the sample fluid are not possible.

Another system for calibrating a sensing electrode is disclosed in U.S. Pat. No. 4,490,236-Petty. This apparatus provides for the measurement of a sample solution with an electrode and for the calibration of the electrode using a test solution. The system includes a cell body having a cavity for receiving a sensing electrode, a reservoir for holding a calibration solution, and a valve provided in the cell body for controlling the flow of the calibration solution to the cavity. The valve is held in a position which prevents flow of the calibration fluid to the cavity by the force of the flowing sample fluid. When the flow of the sample solution is terminated, the valve automatically opens to provide a flow of calibrating solution through the cavity. Thus, calibration is performed using a highly buffered calibrating solution; as a result, this apparatus does not address the problem of the varied response of a pH electrode in highly buffered solutions versus the response of pH electrode in high purity steam cycle water having a minimal buffering capacity.

A variety of dissolved oxygen monitors for continuous on-line operation are available. The most common method for calibrating such dissolved oxygen monitors, most of which are based on a membrane covered polarographic sensor, involves the exposure of the sensor to gas mixtures of known oxygen concentration, including a zero oxygen gas, to establish the monitor zero. Another calibration method involves the measurement of dissolved oxygen in a series of standards and a comparison with a standard, recognized analytical procedure such as the Winkler method. Other suggested methods for calibrating dissolved oxygen monitors include adding oxygen to the fluid sample by electrolytic generation of oxygen. The electrolytic generation of oxygen is reasonable for on-line calibration; however, the addition of an electrolytic cell to a dissolved oxygen monitor significantly increases the cost and complexity of the monitor. Other methods, such as catalase decomposition of hydrogen peroxide, are only useful for off-line calibration and involve elaborate procedures which are difficult to automate or routinely implement in power plants. Thus, most dissolved oxygen monitors in power plants are calibrated at a single point corresponding to 20% oxygen concentration, by exposing the sensor to atmospheric air, and are assumed to have a linear response based on a zero point determined by the zero current output of the polarographic sensor. However, the dissolved oxygen measurements for power plant steam cycle water in most power plants are in the 0–20 ppb range—a measuring range which differs from the calibration point by four orders of magnitude. Therefore, a high degree of accuracy of the monitor in the measuring range cannot be expected, and readings taken with different monitors calibrated by this method are often quite different.

SUMMARY OF THE INVENTION

The present invention is directed to an improved system for remote, on-line calibration of a chemical monitor for monitoring a selected chemical characteristic of, or contaminant in, power plant steam cycle water. A system according to the present invention includes a conditioning system for conditioning an influent fluid sample stream to produce a conditioned fluid sample stream having a predetermined level of the selected chemical characteristic. A sensor of the monitor is exposed to the conditioned fluid sample stream and the response of the sensor is calibrated with respect to the predetermined level of the selected chemical characteristic in the conditioned fluid sample. By using a conditioned fluid sample stream to calibrate the chemical monitor, the present invention eliminates the effects on the response of the sensor of any ionic species in the fluid sample which do not affect the chemical characteristic being monitored. Further, by calibrating the chemical monitor in a conditioned fluid sample stream, the effects of temperature differences between a buffer solution used for calibration and the fluid sample stream are eliminated. Moreover, the conditioned fluid sample stream is provided to the conditioning system by a valve system and the operation of the valve system, and thus the operation of the calibration system of the present invention, can easily be automated and performed remotely.

The on-line calibration system, for calibrating a chemical monitor having a meter, a flow cell, and a sensor provided in the flow cell for sensoring a selected chemical characteristic of a fluid sample stream and generating an output in accordance with the sensed chemical characteristic, according to a first embodiment of the present invention, includes a fluid sample supply line for supplying an influent fluid sample, a conditioning system for conditioning the influent fluid sample stream to produce a conditioned fluid sample stream having a predetermined level of the selected chemical characteristic, a valve system selectively operable to establish first and second fluid sample stream flow paths, the first flow path providing the influent fluid sample stream to the flow cell, and the second flow path providing the influent fluid sample stream to the conditioning system and the conditioned fluid sample stream to the flow cell, and a calibration adjustment system for calibrating the output of the detector, or the response of the meter to the output of the detector, with respect to the predetermined level of the selected chemical characteristic in the conditioned fluid sample stream.

In an on-line calibration system in accordance with a second embodiment of the present invention, the conditioning system comprises a diffusion chamber for conditioning the fluid sample to a predetermined pH value and the chemical monitor comprises a pH monitor. The diffusion chamber includes a container, a pH adjusting reagent provided in the container, and a predetermined length of diffusion tubing immersed in the pH adjusting reagent.

In an on-line calibration system in accordance with a third embodiment of the present invention, the conditioning system comprises diffusion tubing which is exposed to atmospheric air to condition the fluid sample to a predetermined dissolved oxygen concentration and the chemical monitor comprises a dissolved oxygen monitor.

DESCRIPTION OF THE PREFERRED EMBODIMENTS

Figure 1:
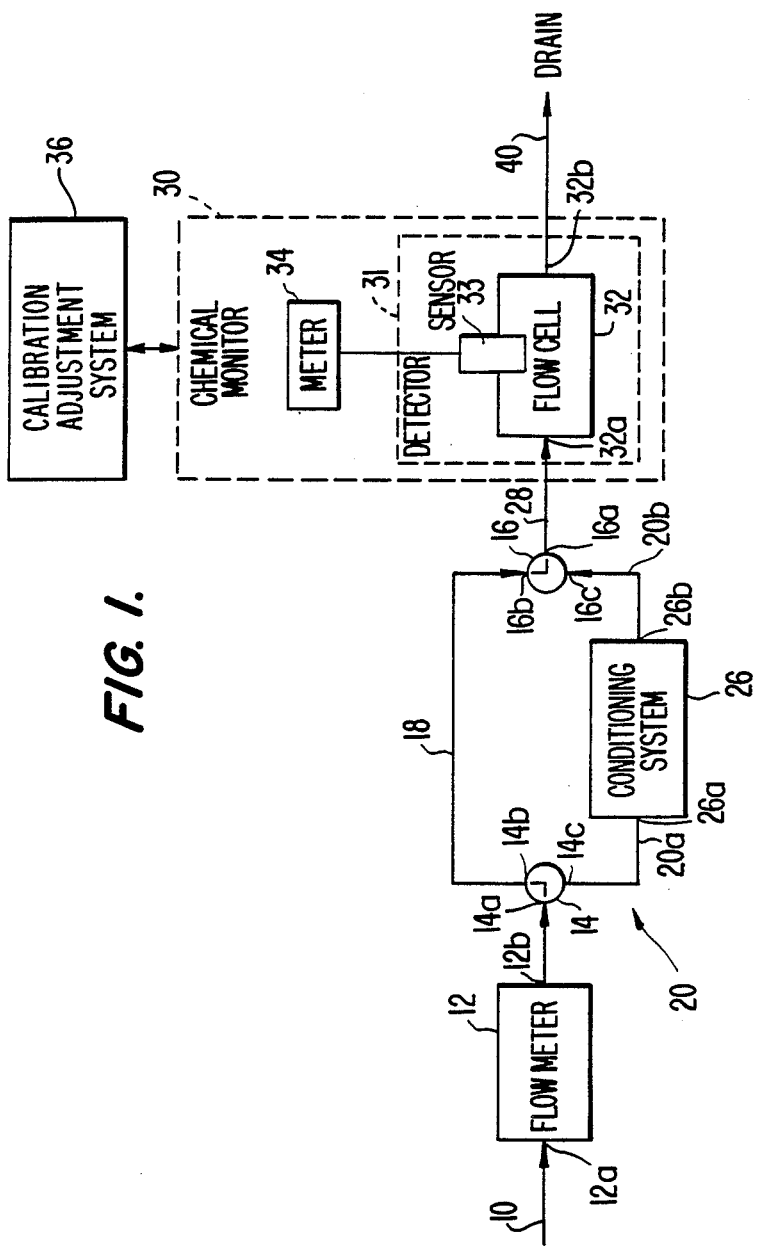
Fig. 1 is a schematic diagram of an on-line chemical monitor calibration system according to the first embodiment of the present invention in conjunction with a first valve system arrangement.

FIG. 1 is a schematic diagram of an on-line chemical monitor calibration system of the first embodiment of the present invention, in conjunction with a first valve system arrangement. The calibration system includes a supply line 10 for supplying an influent fluid sample stream to the calibration system, a flow meter 12 having an input 12a connected to the supply line 10 and an output 12b for supplying the influent fluid sample stream at a predetermined volumetric rate, a first valve system arrangement including a first two-way valve 14 and a second two-way valve 16, first and second parallel fluid lines 18, 20, the second parallel fluid line 20 having first and second portions 20a, 20b, a conditioning system 26 having a first port 26a and a second port 26b, a third fluid line 28, and a chemical monitor 30 for monitoring a selected chemical characteristic of a fluid sample stream.

The first two-way valve 14 has an input 14a in fluid communication with the output 12b of the flowmeter 12, and first and second outputs 14b, 14c. The first two-way valve 14 is selectively operable between a first position for connecting the input 14a and the first output 14b, and a second position for connecting the input 14a and the second output 14c. The second two-way valve has an output 16a, and first and second inputs 16b, 16c. The second two-way valve 16 is selectively operable between a first position for connecting the first input 16b and the output 16a, and a second position for connecting the second input 16c and the output 16a. The first parallel fluid line 18 interconnects the first output 14b of the first valve 14 and the first input 16b of the second valve 16, the first portion of the second parallel fluid line 20a interconnects the second output 14c of the first valve 14 and the first port 26a of the conditioning system 26, and the second portion of the second parallel fluid line 20b interconnects the second port 26b of the conditioning system 26 and the second input 16c of the second valve 16.

The chemical monitor 30 comprises a detector 31 which includes a flow cell 32 and a sensor 33 for sensing the selected chemical characteristic of a fluid sample stream and generating an output in accordance with the sensed chemical characteristic, and a meter 34. The flowcell 32 has first and second ends 32a, 32b and the sensor 33 is provided in the flowcell 32. The meter 34 may be any known readout unit, for example, an analog or digital display, or a strip chart recorder. A third fluid line 28 interconnects the second two-way valve 16 and the first end 32a of the flow cell 32. A calibration adjustment system 36 is connected to the chemical monitor 30, and a drain 40 is connected to the second end 32b of the flow cell 32.

In a monitoring, or operational, mode the first and second two-way valves 14, 16 are both in the first position to establish with the first parallel fluid line 18 a first fluid sample flow stream for providing the influent fluid sample stream to the chemical monitor 30. In a calibration mode, the first and second two-way valves 14, 16 are both in the second position to establish with the first and second portions of the second parallel fluid line 20a, 20b, and the conditioning system 26 a second fluid sample flow stream for providing the influent fluid sample stream to the conditioning system 26, which conditions the influent fluid sample stream to produce a conditioned fluid sample stream having a predetermined level of the selected chemical characteristic, and to provide the conditioned fluid sample stream to the flow cell 32. The calibration adjustment system 36 calibrates the output of the sensor 33, or the response of the meter 34 to the output of the sensor, with respect to the predetermined level of the selected chemical characteristic in the conditioned fluid sample stream, so that the meter 34 provides a reading which corresponds to the predetermined level of selected chemical characteristic. The calibration adjustment system 36 may be, for example, a manual adjustment on the chemical monitor 30 or a microcomputer for remote calibration of the output of the sensor 33.

Figure 2:
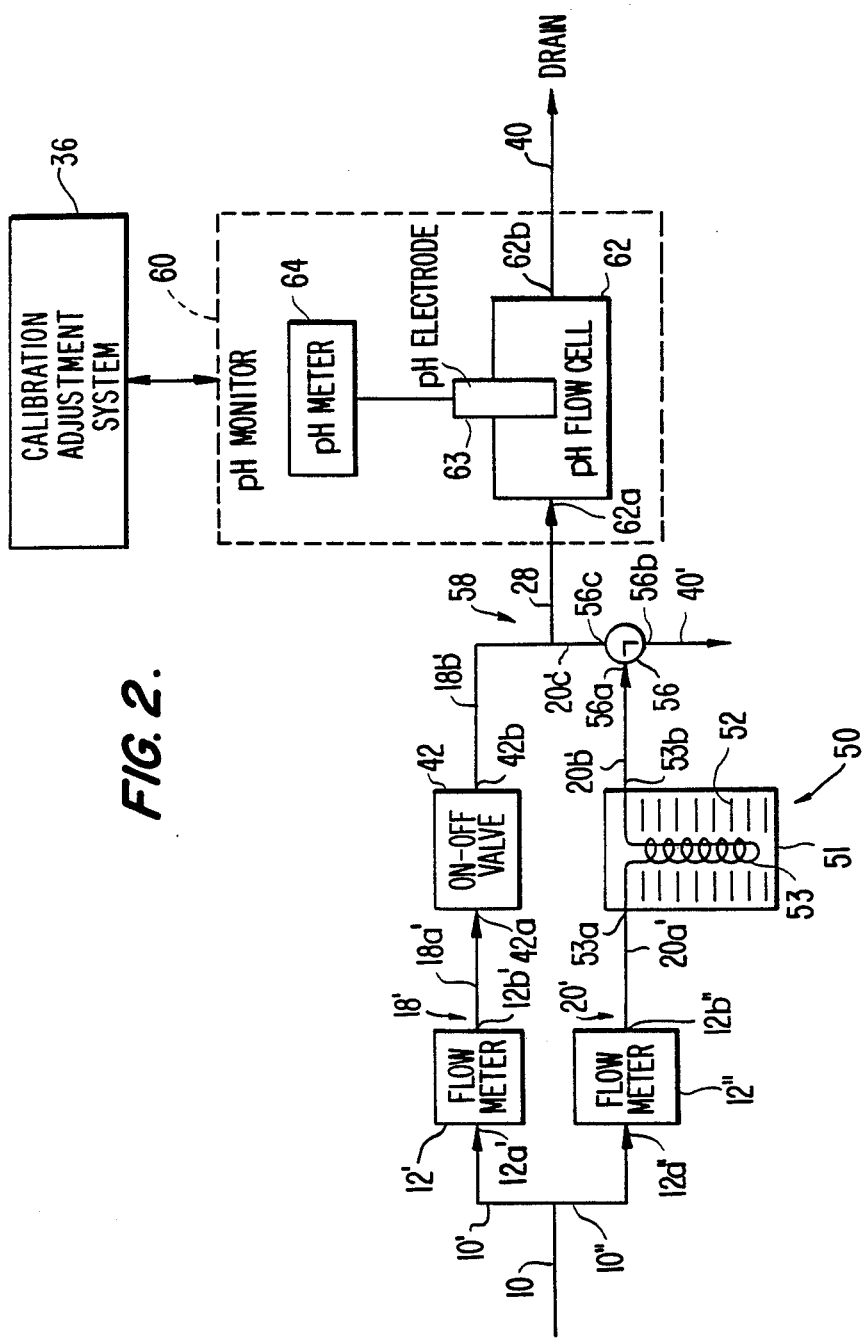
FIG. 2 is a schematic diagram of an on-line pH monitor calibration system according to the second embodiment of the present invention in conjunction with a second valve system arrangement.

FIG. 2 is a schematic diagram illustrating a pH monitor calibration system in accordance with the second embodiment of the present invention, in conjunction with a second valve system arrangement. In the monitoring system employing the second valve system arrangement, the fluid supply line 10 branches into first and second parallel fluid supply lines 10', 10". First and second flowmeters 12', 12", each having an input 12a', 12b" connected to the respective first and second parallel fluid supply lines 10', 10", and an output 12b', 12b", for supplying respective first and second influent fluid sample streams. A first fluid line 18' has first and second first parallel fluid line portions 18a' and 18b', and an on-off valve 42 has an input 42a and an output 42b. The first portion of the first parallel fluid line 18a' interconnects the output 12b' of the first flowmeter 12' and the input 42a of the on-off valve 42, and the second portion of the first parallel fluid line 18b' interconnects the output 42b of the on-off valve and third fluid line 28. A second parallel fluid line 20 has first, second and third portions 20a', 20b' and 20c'.

A diffusion chamber 50 comprises a container 51, for example, a polyethylene bottle, pH adjusting reagent 52, and diffusion tubing 53 having first and second ends 53a, 53b. The diffusion tubing 53 may comprise, for example, Part No. 150061 produced by Orion Research Inc. The first portion of the second parallel fluid line 20a' interconnects the output 12b" of the second flowmeter 12" with the first end 53a of the diffusion tubing 53, to provide the second influent fluid sample stream to the diffusion chamber 50. The influent fluid sample passing through the diffusion chamber 50 is conditioned to a predetermined pH value by the diffusion of the pH adjusting reagent 52 through the diffusion tubing 53 and into the fluid sample stream. Thus, the pH value of the conditioned second fluid sample stream is dependent on the pH adjusting reagent 52 and the length and permeability of the diffusion tubing 53. Diffusion chambers have been used for pH adjustment, to bring the pH of a fluid sample into an optimum range for the operation of ion monitors; however, diffusion chambers have not been used to calibrate pH monitors.

A two-way valve 56 has an input 56a, a first output 56b and a second output 56c, and is selectively operable between a first position connecting the input 56a with the first output 56b, and a second position connecting the input 56a and the second output 56c. The second portion of the second parallel fluid line 20b' interconnects the second end 53b of the diffusion tubing 53 and input 56a of the two-way valve 56, the first output 56b is connected to a drain 40', and the third portion of the second parallel fluid line 20c' interconnects the second output 56c and the third fluid line 28. The second portion of the first parallel fluid line 18b', the third portion of the second parallel fluid line 20c', and the third fluid line 28 comprise a common fluid line 58.

The calibration system shown in FIG. 2 also includes a pH monitor 60. The pH monitor 60 comprises a pH flow cell 62, such as pH flow cell Model 7773 produced by Leeds and Northrup, a pH electrode 63, for example a "Ross" pH electrode produced by Orion Industries, and a pH meter 64, for example a Model 811 pH meter produced by Orion Industries. The pH flow cell 62 has a first end 62a connected to the second portion of the first parallel fluid line 18b' and the third portion of the second parallel fluid line 20c' by the third fluid line 28 and a second end 62b connected to the drain 40. A calibration adjustment system 36 is connected to the pH monitor 60.

In the monitoring mode, the on-off valve 42 is on, or opened, the two-way valve 56 is in the first position, and the on-off valve 42, the first portion of the first parallel fluid line 18', and the common fluid line 58 establish a first fluid sample flow stream for providing the first influent fluid sample stream to the pH monitor 60. To switch from the monitoring mode to the calibration mode, on-off valve 42 is closed, two-way valve 56 is placed in the second position, and the two-way valve 56, the first and second portions of the second parallel fluid line 20a', 20b, the diffusion chamber 50, and the common fluid line 58 establish a second fluid sample flow stream for providing the second influent fluid sample stream to the diffusion chamber 50, and to provide the conditioned second fluid sample stream to the pH flow cell 62. Further, in the monitoring mode the two-way valve 56, the first and second portions of the second parallel fluid line 20a', 20b', and the diffusion chamber 50 establish a third fluid sample stream flow path for providing the second influent fluid sample stream to the diffusion chamber 50, which conditions the second influent fluid sample stream having a predetermined pH, and the conditioned second fluid sample stream to the drain 40'. This arrangement provides a continuous flow of the fluid sample through the diffusion chamber 50 in both the monitoring and calibration modes, which, as discussed below, expedites the calibration procedure.

Figure 3A:
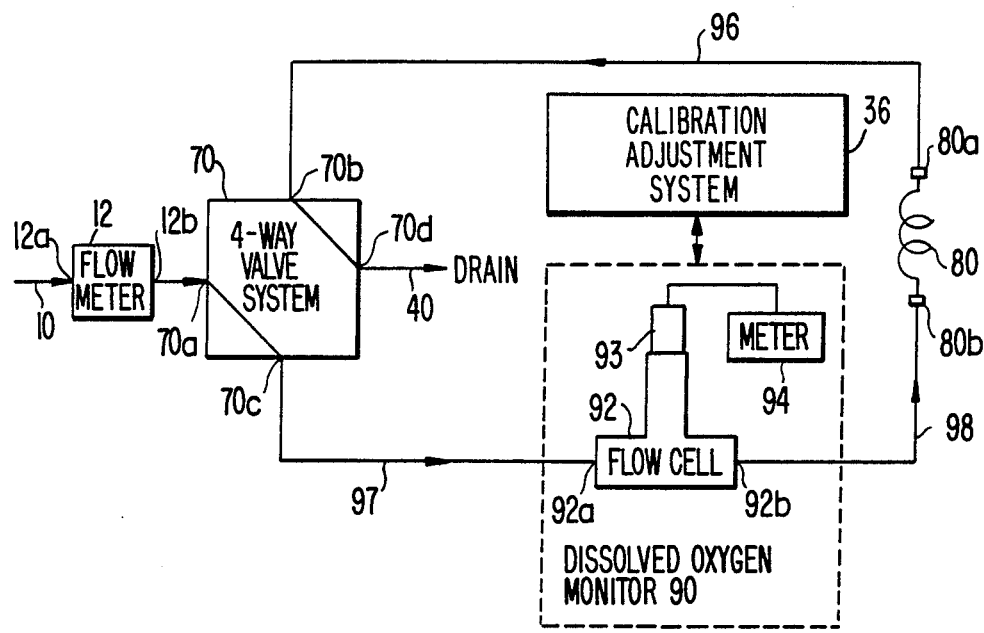
FIGS. 3a and 3b, are schematic diagrams of an on-line dissolved oxygen monitor calibration system according to the third embodiment of the present invention in conjunction with a third valve system arrangement.
Figure 3B:
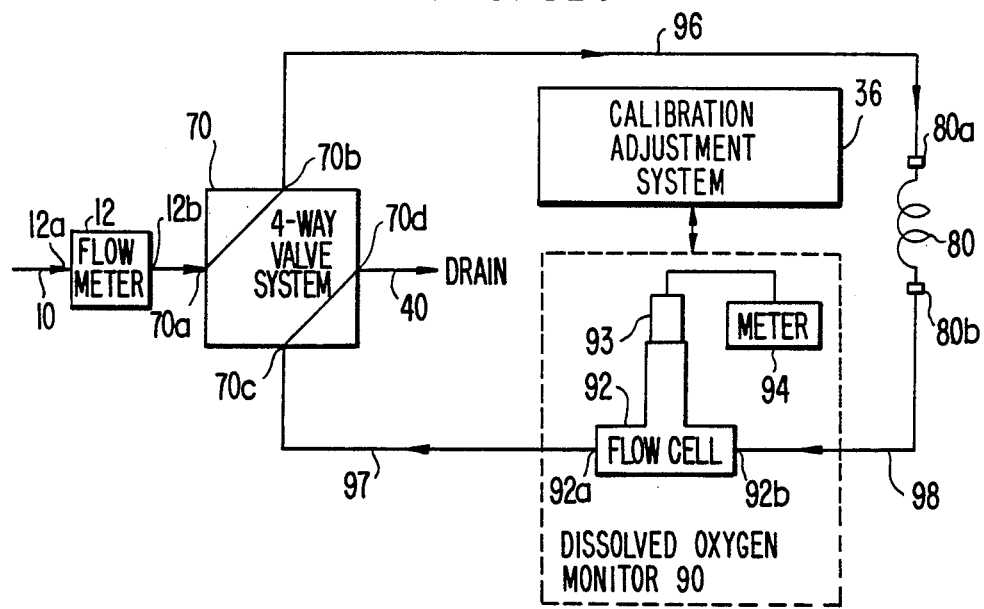

FIGS. 3a and 3b are schematic diagrams illustrating a dissolved oxygen monitor calibration system in accordance with the third embodiment of the present invention, in conjunction with a third valve system arrangement. As shown in FIGS. 3a and 3b, a third valve arrangement includes a four-way valve system 70 having first through fourth ports 70a–70d. The dissolved oxygen monitor calibration system comprises diffusion tubing 80 (Part No. 150061 produced by Orion Industriesl, and a dissolved oxygen monitor 90 including a flow cell 92, a dissolved oxygen sensor 93, for example, a conventional membrane covered polarographic sensor produced by Orbisphere, Model 2110, and a dissolved oxygen meter 94, for example, Model 2606 produced by Orbisphere. The supply line 10 is connected to an input 12a of flowmeter 12 and the output 12b of the flowmeter is connected to the first port 70a of the four-way valve 70. The second port 70b of the four-way valve 70 is in fluid communication with a first end 80a of the diffusion tubing 80 via fluid line 96, the third port 70c of the four-way valve 70 is in fluid communication with a first end 92a of the flow cell 92 via fluid line 97, and the fourth port 70d of the four-way valve system 70 is connected to the drain 40. A second end 80b of the diffusion tubing 80 is in fluid communication with a second end 92b of the flow cell 92 via fluid line 98.

The four-way valve 70 is selectively operable between first and second positions. In an operational or monitoring mode, the four-way valve 70 is in the first position to interconnect the first and third ports 70a, 70c and the second and fourth ports 70b, 70d; thus, in following a first fluid sample stream flow path, the influent fluid sample stream flows to the dissolved oxygen monitor 90 and then to the diffusion tubing 80, and the conditioned fluid sample stream flows to the drain 40. In a calibration mode, the four-way valve 70 is in the second position to interconnect the first and second ports 70a, 70b and the third and fourth ports 70c, 70d; thus, in following a second fluid sample stream flow path the influent fluid sample stream flows to the diffusion tubing 80, and the conditioned fluid sample stream flows to the dissolved oxygen monitor 90 and then to the drain 40. The first and second fluid sample stream flow paths, therefore, are opposite directions of flow through the diffusing tubing 80 and the dissolved oxygen monitor 90. The valve system arrangement illustrated in FIGS. 3a and 3b also provides a continuous flow of the fluid sample through the diffusion tubing 80 in both the monitoring and calibration modes; however, the conditioned fluid sample is supplied to the dissolved oxygen monitor 90 only in the calibration mode.

The amount of dissolved oxygen in steam cycle water is one important aspect of water chemistry with respect to corrosion, as disclosed in related application, Ser. No. 585,063, assigned to the Assignee of the present invention. This related application discloses the injection of oxygen into the condenser system of a steam generating power plant, both above and below the level of the steam cycle water, to determine the amount of dissolved oxygen in the steam cycle water due to air leakage from above and below the steam cycle water level. The present invention is significantly different, in that it is concerned with introducing oxygen into a fluid sample stream to establish a predetermined dissolved oxygen concentration for calibrating a dissolved oxygen monitor.

The pH monitor calibration system, including a diffusion chamber 50 and a pH monitor 60, shown in FIG. 2, and the dissolved oxygen monitor calibration system, including diffusion tubing 80 and the dissolved oxygen monitor 90, shown in FIGS. 3a and 3b, are exemplary. It is, of course, possible to use any of the first through third valve system arrangements shown in FIGS. 1–3 in a dissolved oxygen monitor calibration system or in a pH monitor calibration system. Furthermore, the various valve system arrangements of the calibration system of the present invention are in no way limited to the calibration of pH or dissolved oxygen monitors; rather, they are applicable to any calibration system employing a conditioning system. It is also possible to adapt any of the valve system arrangements for remote control and thus automatic operation.

Figure 8:
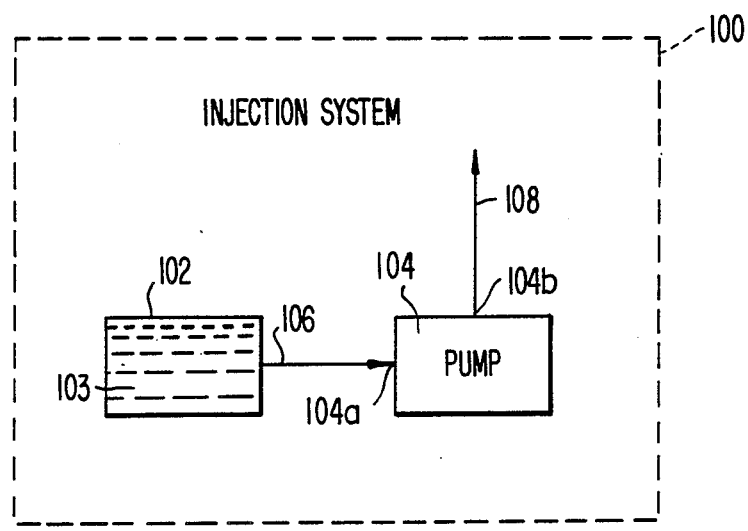
FIG. 8 is a schematic diagram of an injection system for use in conjunction with any of the valve system arrangements.

FIG. 8 is a schematic diagram illustrating an injection system 100, as an example of a conditioning system which may be used in conjunction with any one of the first through third valve system arrangements to calibrate a variety of chemical monitors. The injection system 100 includes a standard solution supply 102 containing a standard solution 103, a pump 104 having an input 104a and an output 104b a fluid line 106 interconnecting the standard solution supply 102 and the input 104a of the pump 104, and an injection line 108 interconnecting the output 104b of the pump 104 with, for example, second parallel fluid line 20 shown in FIG. 1, for injecting the standard solution 103 into the influent fluid sample stream to produce a conditioned sample stream having a predetermined chemical characteristic.

The conditioning system 26 shown in FIG. 1, for example, diffusion chamber 50 shown in FIG. 2, or diffusion tubing 80 shown in FIGS. 3a and 3b, is used to condition the fluid sample to a predetermined chemical characteristic, e.g., pH value or dissolved oxygen concentration. Thus, knowledge of the chemical characteristic of the conditioned fluid sample is essential to the calibration of a monitor. Accordingly, the inventors have performed several experiments to determine the pH of fluid samples conditioned by a diffusion chamber 50 (FIG. 2) and the dissolved oxygen concentration of fluid samples conditioned by diffusion tubing 80 (FIGS. 3a and b).

Figure 4:
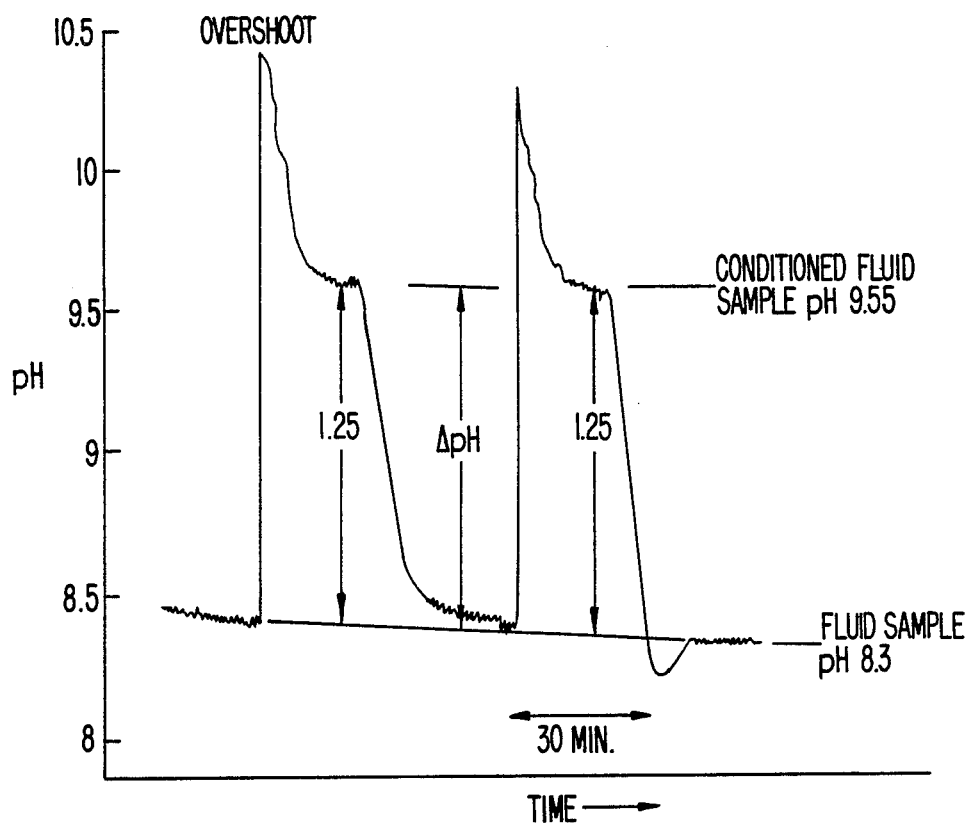
FIG. 4 is a graph for explaining the operation of a pH monitor calibration system having the first valve system arrangement.

FIG. 4 is a graph illustrating the pH conditioning or adjustment, i.e., the pH value of the conditioned fluid sample, achieved with a pH monitor calibration system, i.e., diffusion chamber 50 and a pH monitor 60, shown in FIG. 2, in conjunction with the valve system arrangement illustrated in FIG. 1. The experiments were performed with a diffusion chamber 50 having diffusion tubing 53 (Orion Part No. 150061) four feet in length immersed in a pH adjusting reagent 52 of concentrated ammonium hydroxide (14.8M, 28% NH₃). The graph in FIG. 4 shows that the pH adjustment is excessive, i.e., an overshoot occurs, immediately after the supply of the fluid sample to the pH meter 60 is switched from the first fluid supply line 18 to the second fluid supply line 20 having the diffusion chamber 50 provided therein. The overshoot is caused by a buildup of ammonium hydroxide in the diffusion tubing 53 while the fluid sample in the second fluid line 20, and thus the diffusion chamber 50, is stagnant, i.e., during the period while the fluid sample is being supplied to the pH monitor 60 via the first fluid supply line 18. However, the pH of the conditioned fluid sample stabilized in approximately 30 minutes. Using a flow of approximately 100 cc/min, the pH of the conditioned fluid sample was adjusted from 8.3 to 9.6 after stabilization occurred.

Figure 5:
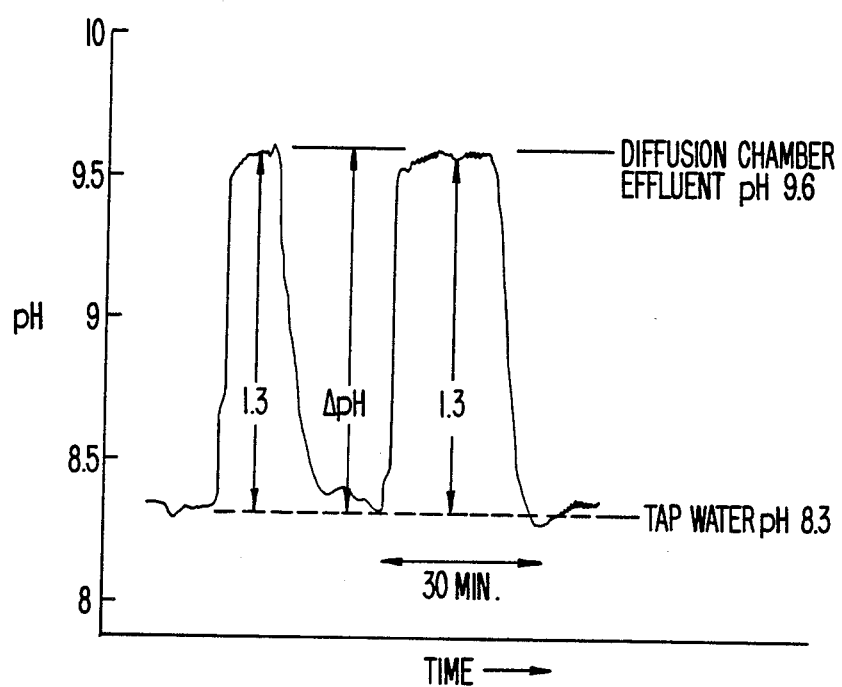
FIG. 5 is a graph for explaining the operation of a pH monitor calibration system having the second valve system arrangement.

The overshoot in the pH adjustment can be eliminated by employing the valve system arrangement illustrated in FIG. 2, which affords a continuous flow of the fluid sample through the diffusion chamber 50 and thus prevents a build-up of the pH adjusting reagent 52, e.g., ammonium hydroxide, in the diffusion tubing 53. Using the same diffusion chamber and flowrate described above in the valve system arrangement shown in FIG. 2, stabilization of the pH adjustment of the conditioned fluid sample occurred in approximately 10 minutes, as shown in FIG. 5.

Figure 6:
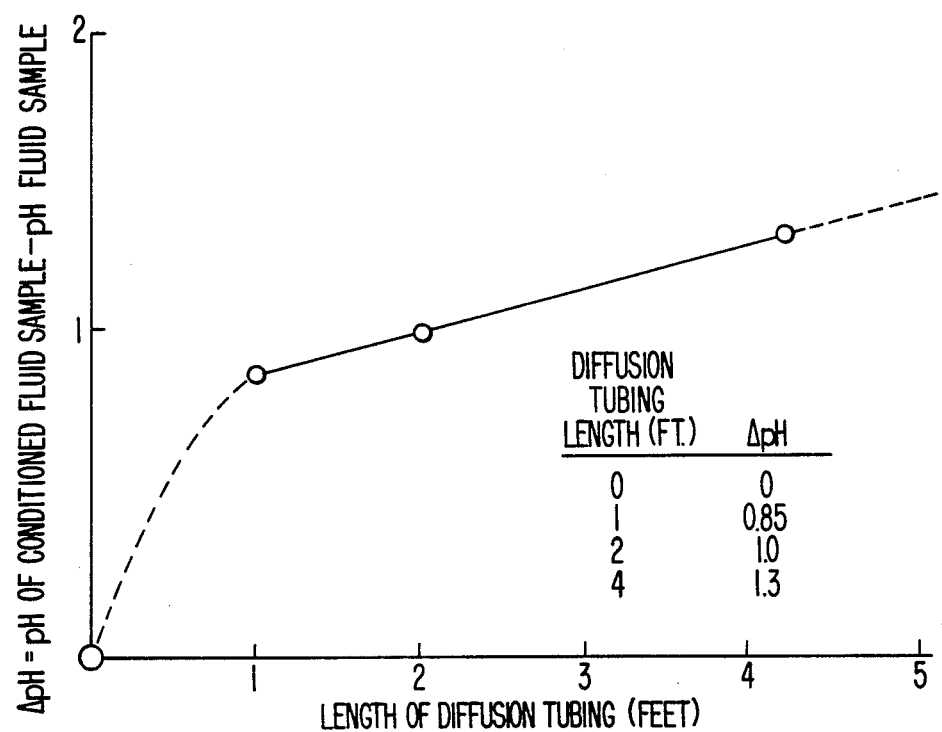
FIG. 6 is a graph for explaining the operation of a pH monitor calibration system.

Experiments have also been performed to determine the relationship between the length of the diffusion tubing 53 and the pH adjustment achieved. FIG. 6 is a graph plotting the length of diffusion tubing 53 versus the pH adjustment ($\Delta$pH) produced by the diffusion chamber 50 with various lengths of diffusion tubing 53, using a constant flow of 100 cc/min and an adjusting reagent 52 of concentrated ammonium hydroxide. As shown in FIG. 6, a relationship exists between the pH adjustment and the length of the diffusion tubing 53 for diffusion tubing lengths greater than approximately one foot.

The use of concentrated ammonium hydroxide as the pH adjusting reagent 52 produces a conditioned fluid sample stream having a pH in the basic, as opposed to acidic, range. It is also possible, however, to produce a conditioned fluid sample having a pH in the acidic range by using, for example, glacial acetic acid as the pH adjusting reagent 52. In laboratory tests, the use of glacial acetic acid and a flow rate of 100 cc/min with a diffusion chamber 50 having four feet of diffusion tubing 53 (Orion Part No. 150061) adjusted the pH of the fluid sample from 7.8 to 3.95. With a diffusion chamber 50 having one foot of diffusion tubing 53 (Orion Part No. 150061) the pH of the fluid sample was adjusted from 7.8 to 5.7.

The change in the dissolved oxygen concentration of the fluid sample is also dependent on the length of the diffusion tubing 80. Since it is contemplated that the conditioning of the fluid sample for calibrating a dissolved oxygen monitor may require conditioned fluid samples having a wide range of dissolved oxygen concentrations, polymers having various permeabilities have been considered for use as the diffusion tubing 80. Polymers with a wide range of permeabilities are available for use as diffusion tubing 80, and representative permeabilities are set forth in Table 1.

TABLE 1

| PERMEABILITIES OF OXYGEN IN POLYMERS | | |
|---|---|---|
| | Permeability $\times 10^{10}$ ($cm^3 \cdot cm/cm^2 \cdot sec$) | |
| Polymer | Gas/Gas | Water/Water |
| Polyethylene | 2.34 | 50.0 |
| Teflon FEP | 3.86 | 105 |
| Teflon | 23.7 | 91.0 |
| Poly(dimethylsiloxane) | 665 | 4000 |

Although the permeabilities presented in Table 1 relate to the permeabilities for gas or water on both sides of the polymer membrane, the range of permeabilities indicates that a wide range of calibration values will be possible. It is noted that these polymers may be the same materials as those used for the oxygen permeable membrane (not shown) in the dissolved oxygen sensor 93.

The preferred manner of calibrating a dissolved oxygen monitor 90 is to provide a conditioned fluid sample to the sensor 93 in a manner identical to that by which a fluid sample is provided to the sensor 93, and to use a conditioned fluid sample having a dissolved oxygen concentration in the range of the dissolved oxygen concentration to be detected by the monitor 90. The range of calibration points can extend from a few parts per billion (ppb) to parts per million (ppm). For example, if a dissolved oxygen monitor 90 is used to detect the dissolved oxygen concentration of boiler feedwater in a steam generating plant, a calibration point of approximately 10 ppb would be appropriate. To maintain equilibrium of the dissolved oxygen level in the conditioned fluid sample and to avoid overshoots in the dissolved oxygen adjustment, it is preferable that the fluid sample continuously flow through the diffusion tubing 80. A continuous flow can be achieved, as previously discussed, with the valve system arrangement illustrated in FIGS. 3a and 3b, wherein the permeable tubing 80 is located downstream from the dissolved oxygen monitor 90 in the monitoring mode, shown in FIG. 3a, and the permeable tubing 80 is located upstream from the dissolved oxygen monitor 90 in the calibration mode, shown in FIG. 3b.

Figure 7:
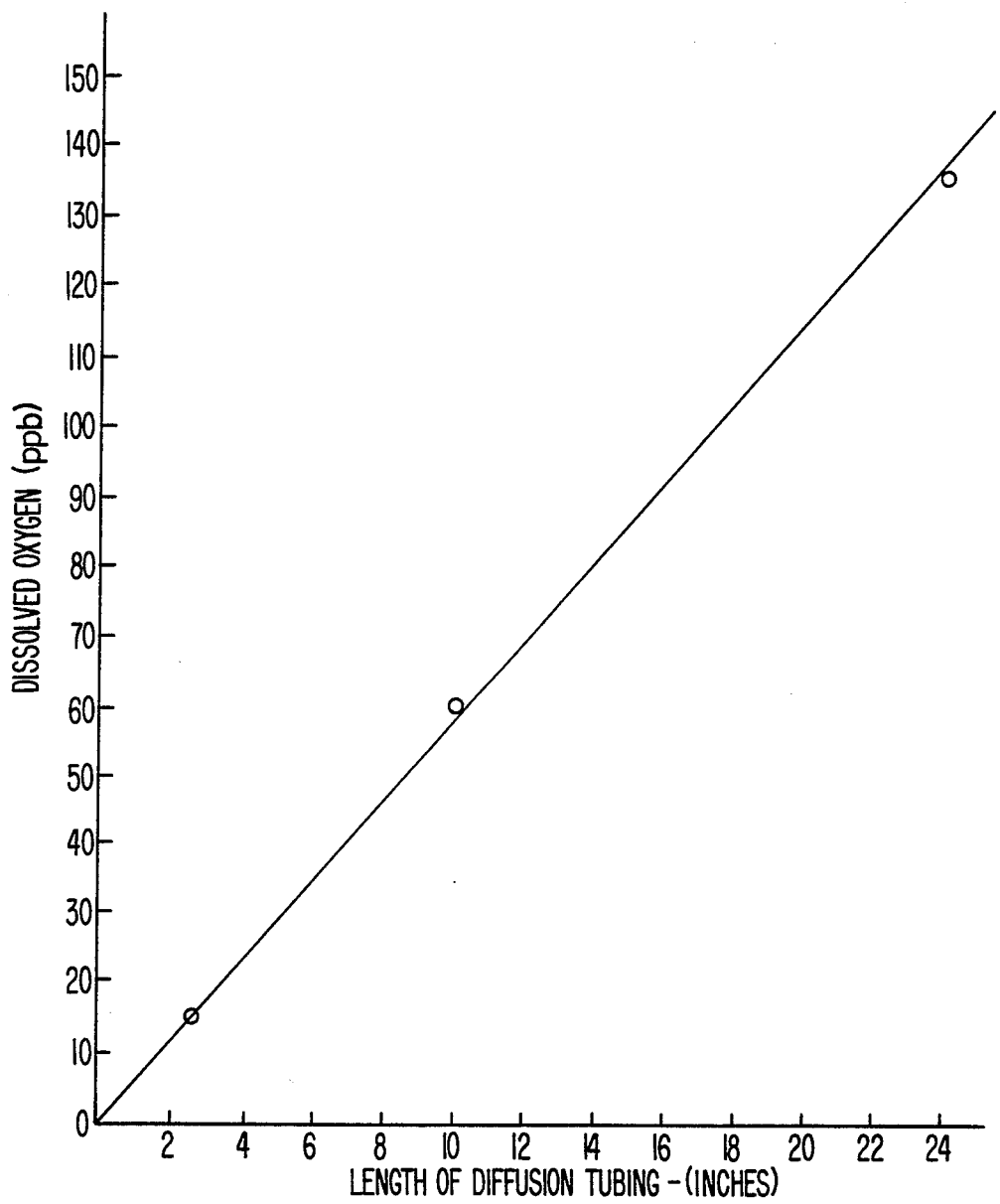
FIG. 7 is a graph for explaining the operation of a dissolved oxygen monitor calibration system.

In laboratory tests performed by the inventors, a dissolved oxygen monitor 90 incorporating an Orbisphere Model 2110 membrane covered polarographic sensor 93 was provided in the calibration system arrangement illustrated in FIGS. 3a and 3b. Prior to testing, the dissolved oxygen monitor 90 was calibrated according to standard procedures set forth by the manufacturer, Orbisphere. The fluid sample was provided by a laboratory deionizing system which delivered high purity water with a dissolved oxygen concentration of approximately 3 ppb. The flow rate through the test system was 300 ml/min, and the diffusion tubing was Orion Part No. 150061 (poly (dimethylsiloxane)). The test system was allowed to come to equilibrium in the operational mode so that the residual dissolved oxygen concentration detected by the dissolved oxygen monitor was 3-4 ppb. The flow was then switched to the calibration mode by the four-way valve 70. The procedure was repeated for diffusion tubing 80 having lengths of 2.5 inches, 10 inches, and 24 inches. The relation between the length of the diffusion tubing 80 and the adjustment of the dissolved oxygen concentration in ppb is shown in the graph of FIG. 7. It can be seen that the relationship between the length of the diffusion tubing 80 and the dissolved oxygen concentration is substantially linear. Thus, a calibration point at any desired dissolved oxygen concentration can be achieved by selecting the appropriate length of diffusion tubing 80.

The present invention, however, is not limited to the calibration of pH and dissolved oxygen monitors or to the calibration of a single monitor. Rather, the present invention relates to systems for on-line calibration of one or more chemical monitors for detecting a wide variety of chemical characteristics in a fluid sample using one or more conditioning systems—particularly, any chemical characteristics for which a conditioned fluid sample stream having predetermined levels of the chemical characteristics can be produced.

All of the examples of the calibration system have used chemical additions to condition the influent fluid sample stream to provide a conditioned fluid sample stream having a predetermined level of the selected chemical characteristics. The present invention, however, is not limited to conditioning by the addition of chemicals but also may employ conditioning which removes chemicals or chemical compounds, or both conditioning by addition and removal of chemicals or chemical compounds. The removal of selected chemicals or chemical compounds to achieve the selected chemical characteristics is especially useful in determining a monitor zero.

What we claim is:

1. A system for on-line calibration of a chemical monitor including a detector for sensing the level of a selected chemical characteristic of a fluid sample stream and producing an output representative of the sensed level of the selected chemical characteristic, comprising:
   means for supplying an influent fluid sample stream at a predetermined volumetric rate;
   means for conditioning the influent fluid sample stream to provide a conditioned fluid sample stream having a predetermined level of the selected chemical characteristic;
   means selectively operable to establish first and second fluid sample stream flow paths, the first flow path providing the influent fluid sample stream to the detector, and the second flow path providing the influent fluid sample stream to the conditioning means and the conditioned fluid sample stream to the detector; and
   means for calibrating the output representative of the sensed level of the selected chemical characteristic with respect to the predetermined level of the selected chemical characteristic in the conditioned fluid sample stream.

2. An on-line calibration system according to claim 1, wherein:
   said conditioning means has first and second ports; and
   said selectively operable means comprises:
      first and second valves, said first valve having an input in fluid communication with said supplying means and first and second outputs and being selectively operable between first and second positions, the first position connecting said input and said first output thereof and the second position connecting said input and said second output thereof, and said second valve having first and second inputs and an output, said output being in fluid communication with the detector, and said second valve being selectively operable between first and second positions, the first position connecting said first input and said output thereof, and the second position connecting said second input and said output thereof,
      a first parallel fluid line interconnecting said first output of said first valve and said first input of the second valve, said first and second valves, in the first positions thereof, being interconnected through said first parallel fluid line and establishing therewith said first fluid sample stream flow path, and
      a second parallel fluid line having first and second portions, said first portion interconnecting said second output of said first valve and said first port of said conditioning means and said second portion interconnecting said second port of said conditioning means and said second input of said second valve, said first and second valves, in the second positions thereof, being interconnected through said respective first and second portions of said second parallel fluid line with said conditioning means and establishing therewith said second fluid sample stream flow path.

3. An on-line calibration system according to claim 1, further comprising:
   a drain;
   said conditioning means having first and second ports;
   said supplying means comprising first and second parallel fluid supply lines and first and second flowmeters, said first and second flowmeters each having an input connected to respective ones of said first and second parallel fluid supply lines and an output, said first and second flowmeters supplying first and second influent fluid sample streams at the same predetermined volumetric rate;
   said selectively operable means being selectively operable to establish first, second and third fluid sample stream flow paths, and comprising:
      an on-off valve having an input and an output, and being selectively operable between open and closed positions,
      a two-way valve having an input, a first output in fluid communication with said drain, and a second output, and being selectively operable between first and second positions, the first position connecting said input and said first output thereof and the second position connecting said input and said second output thereof,
      a first parallel fluid line interconnecting said output of said first flowmeter and said input of said on-off valve,
      a second parallel fluid line having first and second portions, said first portion interconnecting said output of said second flowmeter and said first port of said conditioning means, said second portion interconnecting said second port of said conditioning means and said input of said two-way valve, and
      a common fluid line interconnecting said output of said on-off valve and said second output of said two-way valve with said detector;

said on-off valve, in the open position thereof, interconnecting said first parallel fluid line and said common fluid line and establishing therewith said first fluid sample stream flow path for providing said first influent fluid sample stream to the detector;

said two-way valve, in the second position thereof, interconnecting said second portion of said second parallel fluid line with said common fluid line and establishing therewith, and with said conditioning means and said first portion of said second parallel fluid line, said second fluid sample stream flow path for providing said second influent fluid sample stream to said conditioning means and said conditioned second fluid sample stream to the detector; and said two-way valve, in the first position thereof, interconnecting said second portion of said second parallel fluid line with said drain and establishing therewith, and with said conditioning means and said first portion of said second parallel fluid line, said third fluid sample stream flow path for providing said second influent fluid sample stream to said conditioning means and said conditioned second fluid sample stream to said drain.

4. An on-line calibration system according to claim 1, further comprising:

a drain;

said selectively operable means comprising a four-way valve having first, second, third and fourth ports and being selectively operable between first and second positions, the first position connecting the first and third ports and the second and fourth ports, and the second position connecting the first and second ports and the third and fourth ports;

said first port of said four-way valve being in fluid communication with said supplying means;

said fourth port of said four-way valve being in fluid communication with said drain;

the detector comprising a flow cell having a first end in fluid communication with said third port of said four-way valve, and a second end;

said conditioning means having first and second ports, said first port being in fluid communication with said second port of said four-way valve, and said second port being in fluid communication with the second end of the flowcell; and the first position of said four-way valve establishing said first fluid sample stream flow path and the second position of said four-way valve establishing said second fluid sample stream flow path.

5. An on-line calibration system according to claim 1, wherein said supply means comprises a liquid flowmeter.

6. An on-line calibration system according to claim 1, wherein said conditioning means comprises an injection system for injecting a standard solution into the influent fluid sample stream to provide a conditioned fluid sample stream having a predetermined level of the selected chemical characteristic.

7. A system for on-line calibration of a pH monitor including, a pH flow cell, and a pH electrode provided in the pH flow cell, for monitoring the pH of a fluid sample stream and producing an output representative of the monitored pH, comprising:

means for supplying an influent fluid sample stream at a predetermined volumetric rate;

a diffusion chamber including a container, pH adjusting reagent provided in the container, and a predetermined length of diffusion tubing immersed in the pH adjusting reagent, for conditioning the influent fluid sample stream to provide a conditioned fluid sample stream having a predetermined pH value;

means selectively operable to establish first and second fluid sample stream flow paths, said first flow path providing the influent fluid sample to the pH flow cell, and said second fluid path providing the influent fluid sample stream to the diffusion chamber and the conditioned fluid sample stream to the pH flow cell; and means for calibrating the output representative of the monitored pH with respect to the predetermined pH value of the conditioned fluid sample stream.

8. An on-line calibration system according to claim 7, wherein:

the diffusion tubing has first and second ends; and said selectively operable means comprises:

first and second valves, said first valve having an input in fluid communication with said supplying means and first and second outputs and being selectively operable between first and second positions, the first position connecting said input and said first output thereof and the second position connecting said input and said second output thereof, said second valve having first and second inputs and an output in fluid communication with the pH flow cell, and said second valve being selectively operable between first and second positions, the first position connecting said first input and said output thereof and the second position connecting said second input and said output thereof, a first parallel fluid line interconnecting said first output of said first valve and said first input of the second valve, said first and second valves, in the first positions thereof, being interconnected through said first parallel fluid line and establishing therewith said first fluid sample stream flow path, and a second parallel fluid line having first and second portions, said first portion interconnecting said second output of said first valve and said input of said diffusion tubing, said second portion interconnecting said second end of said diffusion tubing and said second input of said second valve, said first and second valves, in the second positions thereof, being interconnected through said respective first and second portions of said second parallel fluid line with said diffusion tubing and establishing therewith said second fluid sample stream flow path.

9. An on-line calibration system according to claim 7, further comprising:

a drain;

said diffusion tubing having first and second ends;

said supplying means comprising first and second parallel fluid supply lines and first and second flowmeters, said first and second flowmeters each having an input connected to respective ones of said first and second parallel fluid supply lines and an output, said first and second flowmeters supplying first and second influent fluid sample streams at the same predetermined volumetric rate;

said selectively operable means being selectively operable to establish first, second and third fluid sample stream flow paths, and comprising:
an on-off valve having an input and an output, and being selectively operable between open and closed positions,
a two-way valve having an input, a first output in fluid communication with said drain, and a second output, selectively operable to establish first and second positions, the first position connecting said input and said first output thereof and the second position connecting said input and said second output thereof,
a first parallel fluid line interconnecting said output of said first flowmeter and said input of said on-off valve,
a second parallel fluid line having first and second portions, said first portion interconnecting said output of said second flowmeter and said first end of said diffusion tubing, said second portion interconnecting said second end of said diffusion tubing and said input of said two-way valve, and
a common fluid line interconnecting said output of said on-off valve and said second output of said second valve with the pH flow cell;
said on-off valve, in the open position thereof, interconnecting said first parallel fluid line and said common fluid line and establishing therewith said first fluid sample stream flow path for providing said first influent fluid sample stream to the detector;
said two-way valve, in the second position thereof, interconnecting said second portion of said second parallel fluid line with said common fluid line and establishing therewith, and with said diffusion tubing and said first portion of said second parallel fluid line, said second fluid sample stream flow path for providing said second influent fluid sample stream to said diffusion tubing and said conditioned second fluid sample stream to the pH flow cell; and
said two-way valve, in the first position thereof, interconnecting said second portion of said second parallel fluid line with said drain and establishing therewith, and with said diffusion tubing and said first portion of said second parallel fluid line, said third fluid sample stream flow path for providing said second influent fluid sample stream to said diffusion tubing and said conditioned second fluid sample stream to said drain.

10. An on-line calibration system according to claim 7, further comprising:
a drain;
said selectively operable means comprising a four-way valve having first, second, third and fourth ports and being selectively operable between first and second positions, the first position connecting the first and third ports and the second and fourth ports, and the second position connecting the first and second ports and the third and fourth ports;
said first port of said four-way valve being in fluid communication with said supplying means;
said fourth port of said four-way valve being in fluid communication with said drain;
the pH flow cell having a first end in fluid communication with said third port of said four-way valve, and a second end;
said diffusion tubing having a first end in fluid communication with said second port of said four-way valve, and a second end in fluid communication with the second end of the pH flow cell; and
the first position of said four-way valve establishing the first fluid sample stream flow path and the second position of said four-way valve establishing the second fluid sample stream flow path.

11. An on-line calibration system according to claim 7, wherein the supply means comprises a flowmeter.

12. A system for on-line calibration of a dissolved oxygen monitor including a flow cell, and a sensor provided in the flow cell, for monitoring the dissolved oxygen concentration of a fluid sample stream and producing an output representative of the monitored dissolved oxygen concentration, comprising:
means for supplying an influent fluid sample stream at a predetermined volumetric rate;
diffusion tubing for conditioning the influent fluid sample stream to provide a conditioned fluid sample stream having a predetermined dissolved oxygen concentration;
means selectively operable to establish first and second fluid sample stream flow paths, the first flow path providing the influent fluid sample stream to the flow cell, and the second flow path providing the influent fluid sample stream to the diffusion tubing and the conditioned fluid sample stream to the flow cell; and
means for calibrating the output representative of the monitored dissolved oxygen concentration with respect to the predetermined dissolved oxygen concentration of the conditioned fluid sample stream.

13. An on-line calibration system according to claim 12, further comprising:
a drain;
said selectively operable means comprising a four-way valve having a first, second, third and fourth ports and being selectively operable between first and second positions, the first position connecting said first and third ports and said second and fourth ports, and the second position connecting said first and second ports and said third and fourth ports;
said first port of said four-way valve being in fluid communication with said supplying means;
said fourth port of said four-way valve being in fluid communication with said drain;
the flow cell having a first end in fluid communication with said third port of said four-way valve, and a second end;
said diffusion tubing having a first end in fluid communication with said second port of said four-way valve, and a second end in fluid communication with the second end of the flow cell; and
the first position of said four-way valve establishing the first fluid sample stream flow with and the second position of said four-way valve establishing the second fluid sample stream flow path.

14. A system for on-line calibration of a pH monitor including, a pH flow cell, and a pH electrode provided in the pH flow cell, for monitoring the pH of a fluid sample stream and generating an output in accordance with the detected pH, and a meter for displaying the monitored pH in accordance with the output of the pH electrode, comprising:
a flowmeter having an input for receiving an influent fluid sample stream, and an output for supplying the influent fluid sample stream at a predetermined volumetric rate;

a diffusion chamber, including a container, a pH adjusting reagent provided in the container, and a predetermined length of diffusion tubing having first and second ends and being immersed in the pH adjusting reagent, for conditioning the influent fluid sample stream to provide a conditioned fluid sample stream having a predetermined pH value;

a first valve having an input in fluid communication with said output of said flow meter, and first and second outputs, and said first valve being selectively operable between first and second positions, the first position connecting said input and said first output thereof and the second position connecting said input and said second output thereof;

a second valve having first and second inputs and an output and being selectively operable between first and second positions, the first position connecting said first input and said output thereof and the second position connecting said second input and said output thereof;

a first parallel fluid line interconnecting said first output of aaid first valve and said first input of said second valve, said first and second valves, in the first positions thereof, being interconnected through said first parallel fluid line and establishing therewith a first fluid sample stream flow path for providing the influent fluid sample stream to the pH flow cell;

a second parallel fluid line having first and second portions, said first portion interconnecting said second output of said first valve and said first end of said diffusion tubing, said second portion interconnecting said second end of said diffusion tubing and said second input of said second valve, said first and second valves, in the second positions thereof, being interconnected through said respective first and second portions of said second parallel fluid line with said diffusion tubing and establishing therewith a second fluid sample stream flow path for providing the influent sample stream to the diffusion tubing and the conditioned fluid sample stream to the pH flow cell; and a calibration adjusting system for calibrating the pH displayed by the meter with respect to the predetermined pH value of the conditioned fluid sample stream.

15. A system for on-line calibration of a dissolved oxygen monitor including a flow cell having first and second ends, a sensor for detecting the dissolved oxygen concentration of a fluid sample stream and generating an output in accordance with the detected dissolved oxygen concentartion, anc a meter for oisplaying tne monitored dissolved oxygen concentration in accordance with the output of the sensor, comprising:

a flowmeter having an input for receiving an influent fluid sample stream and an output for supplying the influent fluid sample stream at a predetermined volumetric rate;

diffusion tubing having a predetermined length, a first end, and a second end in fluid communication with the second end of the flow cell, for conditioning the influent fluid sample stream to produce a conditioned fluid sample stream having a predetermined dissolved oxygen concentration;

a drain;

a four-way valve having a first port in fluid communication with the output of said flowmeter, a second port in fluid communication with the first end of said diffusion tubing, a third port in fluid communication with the first end of the flow cell, and a fourth port in fluid communication with said drain, and being selectively operable between first and second positions, the first position connecting said first and third ports and said second and fourth ports to provide the influent fluid sample stream to the flow cell, and the second position connecting said first and second ports and said third and fourth ports to provide the influent fluid sample stream to said diffusion tubing and the conditioned fluid sample stream to the flow cell; and a calibration adjustment system for calibrating the dissolved oxygen concentration displayed by the meter with respect to the predetermined dissolved oxygen concentration of the conditioned fluid sample stream.

* * * * *